(12) United States Patent
Cleary et al.

(10) Patent No.: US 6,696,586 B1
(45) Date of Patent: Feb. 24, 2004

(54) BIS AU(I) SENSITIZERS AND THEIR SYNTHESIS

(75) Inventors: Brian P. Cleary, Webster, NY (US); Roger Lok, Rochester, NY (US); Weimar W. White, Canaseraga, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/214,031

(22) Filed: Aug. 7, 2002

(51) Int. Cl.$^7$ .............................. C07F 1/12; G03C 1/06
(52) U.S. Cl. ..................... 556/113; 556/11; 548/106; 548/108; 549/3; 549/210; 430/605
(58) Field of Search ............................. 556/111, 113; 548/106, 108; 549/3, 210; 430/605

(56) References Cited

U.S. PATENT DOCUMENTS

| | | | |
|---|---|---|---|
| 3,503,749 A | 3/1970 | Tavernier et al. | 96/107 |
| 5,049,484 A | 9/1991 | Deaton | 430/605 |
| 5,220,030 A | 6/1993 | Deaton | 548/105 |
| 5,252,455 A | 10/1993 | Deaton | 430/605 |
| 5,391,727 A | 2/1995 | Deaton | 540/1 |
| 5,620,841 A | 4/1997 | Lok et al. | 430/600 |
| 5,700,631 A | 12/1997 | Lok et al. | 430/605 |
| 5,939,245 A | 8/1999 | Lok et al. | 430/567 |
| 5,945,270 A | 8/1999 | Lok et al. | 430/605 |
| 6,365,746 B1 | 4/2002 | Lok et al. | 548/106 |

OTHER PUBLICATIONS

JP Abstract 8069053, Mar. 12, 1996.
U.S. application Ser. No. 10/213,992 of Roger Lok et al, "Silver Halide Photographic Elements Containing Bis Au(I) Sensitizers".

*Primary Examiner*—Porfirio Nazario-Gonzalez
(74) *Attorney, Agent, or Firm*—Sarah Meeks Roberts

(57) ABSTRACT

This invention relates to an organothiosulfonato Au(I) complex having the formula

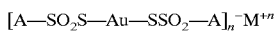

$$[A-SO_2S-Au-SSO_2-A]_n^- M^{+n}$$

wherein
M is a cationic counter ion;
A is a substituted or unsubstituted organic group;
and n is 1 to 4; and wherein the compound is symmetrical. It further relates to the synthesis of said compounds.

28 Claims, No Drawings

BIS AU(I) SENSITIZERS AND THEIR SYNTHESIS

FIELD OF THE INVENTION

This invention relates organothiosulfonato Au(I) complexes and methods of preparing the organothiosulfonato Au(I) complexes. These compounds are particularly useful as sensitizers for silver halide emulsions. It is also anticipated that these compounds may be useful in the pharmaceutical industry.

BACKGROUND OF THE INVENTION

Color photographic paper is used in a wide variety of photoprocessing machines, which include large-scale processors capable of providing large volumes of photographic prints under conditions of continuous operation, and small-scale processors that are used to produce smaller volumes of photographic prints under conditions of discontinuous operation. These machines are known to differ widely in mechanical design, and the operating conditions for these processors vary widely in ambient temperature and humidity due to the wide variety of environments for use.

To provide a color photographic paper that serves all the different machines and conditions and is tolerant of the wide fluctuations in environment, one must address the variation of color paper performance to changes in heat and humidity at the site of operation. One aspect of these variations relates to the sensitivity of the photographic paper to changes in temperature, otherwise known as heat sensitivity. It is desirable to make photographic materials that are invariant to any changes in environmental temperature, such that the photographic response does not change when the ambient temperature fluctuates during the course of processor operations. Alternatively, satisfactory results can be achieved when the photographic response is neutral with respect to changes in environmental temperature, that is, although the photographic material may have a different response as the temperature changes, the changes are not noticeable to the operator as the effects of temperature in each of the constituent layers are synchronized to annul the effect of the temperature changes. It is known that heat sensitivity of the photographic material is critical to its acceptability for use, and that changes in heat sensitivity can occur when changes are made in the process of manufacturing. Thus, it is highly desirable that manufacturing changes do not degrade heat sensitivity.

There has been considerable effort devoted to improving the sensitivity of silver halide crystals to actinic radiation and thereby increasing the sensitivity of the photographic elements in which they are contained. In this regard, photographic chemists have attempted to vary the components of, or the processes for making, silver halide emulsions. One particularly preferred means to improve sensitivity has been to chemically sensitize photographic emulsions with one or more compounds containing labile atoms of gold, sulfur, selenium or the like. Examples of chemically sensitized photographic silver halide emulsion layers are described in, for example, *Research Disclosure*, Item No. 308119, December 1989, Section III, and the references listed therein. (*Research Disclosure* is published by Kenneth Mason Publications Ltd, Dudley Annex, 12a North Street, Emsworth, Hampshire PO 10 7DQ, England.)

One common gold sensitizer used in the sensitization of silver halide emulsions is aurous sulfide, which is made as a colloidal gelatin dispersion, the exact composition of which is not well characterized. This gold sulfide dispersion can give rise to lot-to-lot variability and undesirable and inconsistent sensitometric performance. The source of this variability may come from side reactions in the preparation of this highly insoluble solid since these reactions produce species, which may be photographically active. Further, because of the highly insoluble nature of gold sulfide, most of the sensitizer added is, in fact, unused during the sensitization. The remaining sensitizer left in the gel/silver halide matrix can affect sensitometry.

Other organo gold compounds have been described. For example, U.S. Pat. No. 3,503,749 describes the use of water soluble Au(I) thiolate salts comprising one Au atom ligated to one sulfur containing ligand, and JP 8069075 discusses the use of organic gold sulfide compounds in the sensitization to give low fogging and high contrast silver halide photographic materials. U.S. Pat. No. 5,220,030 teaches the use of Au(I) compounds with bis mesoionic heterocycles; U.S. Pat. Nos. 5,252,455 and 5,391,727 disclose the use of Au(I) macrocyclic cationic sensitizers; and U.S. Pat. No. 5,049,484 teaches the use of Au(I) sensitizers having a Au atom ligated to the nitrogen atom of heterocyclic rings. These gold compounds, while being useful sensitizers, are somewhat lacking in solution stability. U.S. Pat. No. 5,945,270 describes the use of water soluble organomercapto Au(I) complex as being useful sensitizers in silver chloride emulsions.

Gold complexes containing the thiosulfonato group have been reported. U.S. Pat. No. 5,620,841 discloses the use of gelatin dispersions of a Au(I) thiosulfonato sensitizer with two different ligands at least one of which is mesoionic. U.S. Pat. No. 5,700,631 teaches the use of gelatin dispersions of Au(I) thiosulfonato sensitizers with two different ligands at least one of which is a thioether group. U.S. Pat. No. 5,939,245 teaches the sensitization of silver chloride emulsions by Au(I) thiosulfonato sensitizers the composition of which contains a thiourea moiety.

Regardless of the extensive activity in this area, there is a continuing need for Au (I) compounds that are effective sensitizers and that are stable, water soluble and well characterized. Further, such compounds must be easily manufacturable from readily available starting materials.

SUMMARY OF THE INVENTION

This invention provides organothiosulfonato Au(I) complexes having the formula

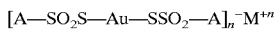

wherein
  M is a cationic counterion;
  A is a substituted or unsubstituted organic group;
  and n is 1 to 4; and wherein the compound is symmetrical.

The novel organothiosulfonato Au(I) complexes of this invention have numerous advantages. They are highly effective sensitizers for silver halide emulsions. Although unproven, they may also be useful in the pharmaceutical industry. The compounds are water soluble. Because of the water solubility of these complexes, the use of costly and time consuming preparation of gel dispersions is unnecessary. Further, there is no need to use large volumes of water for dissolving the complexes.

Unlike prior mixed-ligand gold compounds, the two Au ligands in the complexes of this invention are identical, thus reducing the complexity of preparation. Further, the complexes may utilize commercially available starting materials.

Another advantage is that the preparation of the gold complexes of the present invention does not utilize dangerous explosive gold fulminates or large quantities of organic solvents.

The organothiosulfonates used in the preparation of the Au(I) complexes may include the numerous thiosulfonate antifoggants/stabilizers. Because of the sensitizing, antifogging, and stabilizing properties of these thiosulfonate ligands, the Au(I) sensitizers derived from these ligands may also show speed enhancing and antifogging/stabilizing effects in addition to their sensitizing properties. The compounds may particularly have improved heat sensitivity over prior art sensitizers.

DETAILED DESCRIPTION OF THE INVENTION

The organothiosulfonato Au(I) complexes of the invention may be represented by the formula

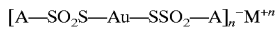

$$[A-SO_2S-Au-SSO_2-A]_n^- M^{+n}$$

with the complex being symmetrical around the atomic Au. M is a cationic counter ion. Preferably M is an alkali or alkali earth metal, for example, lithium, sodium, potassium, rubidium, cesium, magnesium, calcium, strontium or barium, or an ammonium cation, for example, a tetrabutyl or tetraethyl ammonium group. M may also be, for example, $Fe^{+4}$ or $Mn^{+3}$. n is 1 to 4, preferably 1 or 2. A is a substituted or unsubstituted organic radical. Preferably A is an aliphatic, (cyclic or acyclic), aromatic or heterocyclic group. When A is an aliphatic group, preferably it is a substituted or unsubstituted aliphatic group having 1 to 20 carbon atoms, and more preferably having 1 to 8 carbon atoms. Examples of appropriate groups include alkyl groups such as methyl, ethyl, propyl, butyl, pentyl, hexyl, octyl, 2-ethylhexyl, decyl, dodecyl, hexadecyl, octadecyl, cyclohexyl, isopropyl, and t-butyl groups.

The heterocyclic groups may be substituted or unsubstituted 3- to 15-membered rings with at least one atom selected from nitrogen, oxygen, sulfur, selenium, and tellurium in the ring nucleus, with nitrogen being preferred. Examples of heterocyclic groups include the radicals of pyrrolidine, piperidine, pyridine, tetrahydrofuran, thiophene, oxazole, thiazole, imidazole, benzothiazole, benzoxazole, benzimidazole, selenazole, benzoselenazole, tellurazole, triazole, benzotriazole, tetrazole, oxadiazole, or thiadiazole rings.

The preferred aromatic groups have from 6 to 20 carbon atoms. More preferably, the aromatic groups have 6 to 10 carbon atoms and include, among others, phenyl and naphthyl groups. Preferably, the aromatic group is a phenyl ring.

These groups may have substituent groups. Unless otherwise specifically stated, substituent groups may include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be bonded to the remainder of the molecule by an atom of carbon, silicon, oxygen, nitrogen, phosphorous, or sulfur. Suitable substituents for A include, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3- to 7-membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy. One particularly suitable substituent for A is a methyl group. Specific examples of the Au(I) complexes include, but are not limited to;

  (A)

  (B)

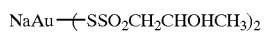  (C)

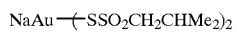  (D)

  (E)

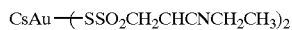  (F)

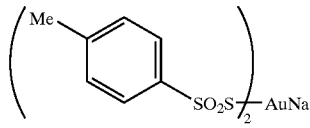  (G)

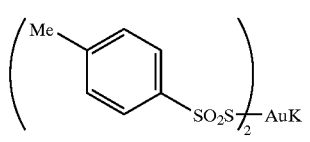  (H)

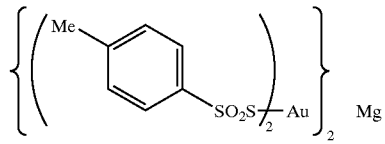  (I)

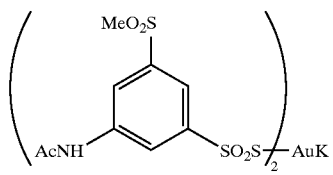  (J)

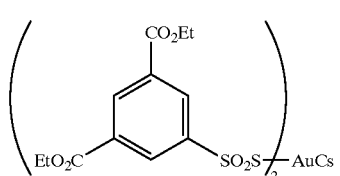  (K)

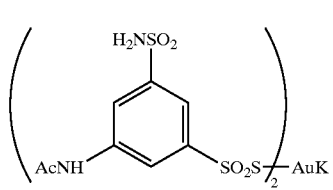  (L)

-continued

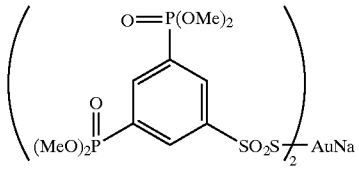  (M)

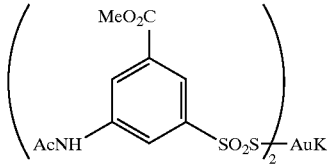  (N)

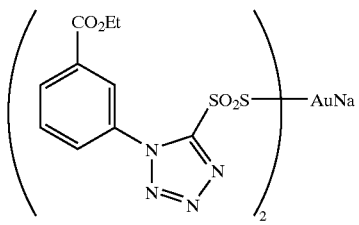  (O)

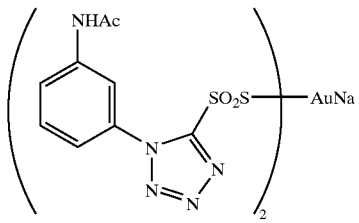  (P)

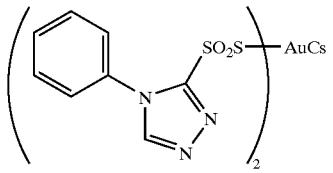  (Q)

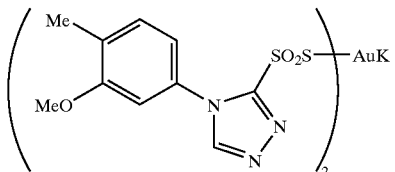  (R)

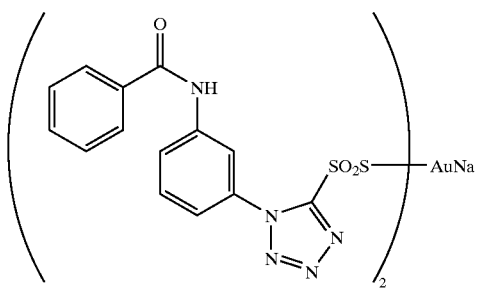  (S)

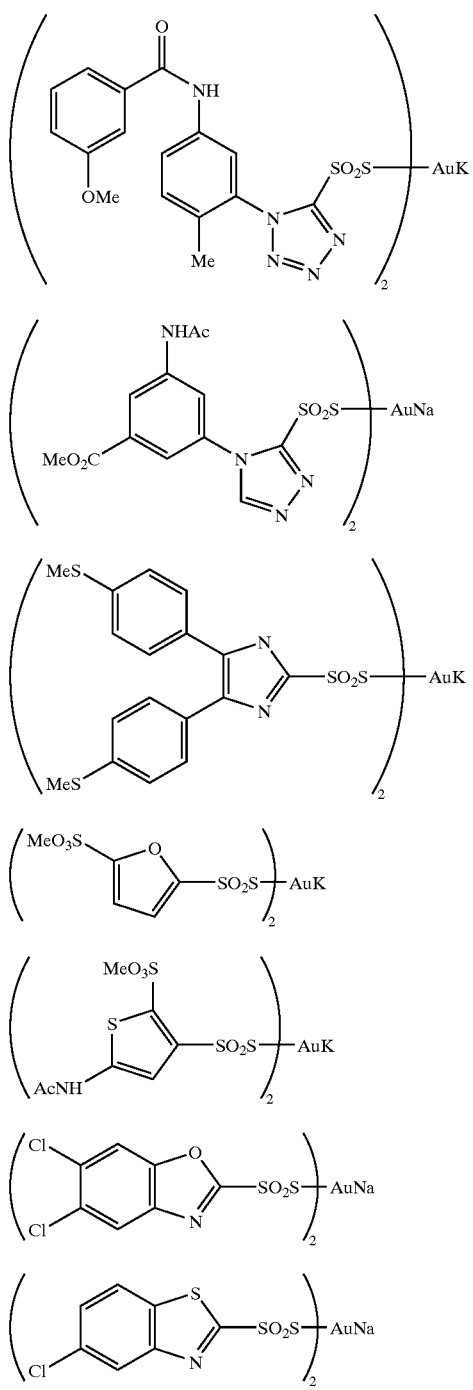

One particularly suitable complex is Compound G, sodium bis (4-methylphenylthiosulfonato)aurate(I).

One of the advantages of the complexes of this invention is their solubility in water. Preferably they have a solubility at 22° C. of 2 g/L, more preferably 5 g/L, and most preferably 10 g/L. Particularly suitable compounds have a solubility of greater than 20 g/L.

The organothiosulfonato Au(I) complexes preferably are manufactured by reacting a Au(I) complex with an organothiosulfonato ligand and isolating the resulting organothiosulfonato Au(I) complex from the reaction mixture. Suitable Au(I) complexes for use in this process are those having a more positive redox potential than the desired organothiosulfonato Au(I) complex, thus allowing for the easy replacement of the ligand. Such compounds are known to those skilled in the art. Examples of some useful Au(I) complexes include $AuCl_2^-$, $AuBr_2^-$, $Au(MeS-CH_2-CH_2-CHNH_2COOH)_2^+$, $Au(C_3H_3N_2-CH_2-CH_2-NH_2)_2^+$, $Au(CNS)_2^-$, AuCl, Au Br, AuI, or $Au(NH_3)_2^+$, with AuCl being particularly suitable. AuI is the least preferred of the above complexes.

Because the Au(I) complexes can be somewhat unstable, it is preferred to prepare them immediately before use by reacting a Au(III) compound with a stoichiometric amount of a reducing agent. The Au(III) compound can be any such compound which can be reduced to a stable Au(I) complex. Many of these compounds are commercially available. Examples of suitable compounds include $AuI_3$, $KAuBr_4$, $KAuCl_4$, $AuCl_3$, and $HAuCl_4$. The reducing reagents may be, among others, tetrahydrothiophene, 2,2'-thiodiethanol, thiourea, N,N'-tetramethylthiourea, alkyl sulfides (e.g., dimethylsulfide, diethylsulfide, diisopropylsulfide), thiomorpholin-3-one, sulfite, hydrogen sulfite, uridine, uracil, alkali hydrides, alkyl alcohols and iodide. (Uson, R.; Laguna, A.; Laguna, M. *Inorg. Synth.* 1989, 26, 85–91; Al-Saady, A. K.; McAuliffe, C. A.; Parish, R. V.; Sandbank, J. A. *Inorg. Synth.* 1985, 23, 191–194; Ericson, A.; Elding, L. I.; Elmroth, S. K. C.; *J. Chem. Soc., Dalton Trans.* 1997, 7, 1159–1164; Elding, L. I.; Olsson, L. F. *Inorg. Chem.* 1982, 21, 779–784; Annibale, G.; Canovese, L.; Cattalini, L.; Natile, G. *J. Chem. Soc., Dalton Trans.* 1980, 7, 1017–1021). In some instances the reduction can be performed in the presence of a stabilizing agent such as the chloride anion (Miller, J. B.; Burmeister, J. L. *Synth. React. Inorg. Met.-Org. Chem.* 1985, 15, 223–233). In some instances it may be desirable to isolate the resulting Au (I) compound, i.e., to avoid undesirable side reactions. For example, in the case of AuI, removal of excess iodine is desirable to avoid deleterious sensitometric effects. Depending on the stability of the resulting Au(I) compound, however, its isolation may not be practical.

It is preferable that the Au(I) complex/organothiosulfonato reaction be completed in an aqueous system, however, this is not imperative. In general, the procedure requires no more than the mixing or stirring of the reagents for a short time, preferably at a temperature slightly above room temperature. In one preferred embodiment the Au(I) compound is treated with at least two equivalents of a water soluble organo thiosulfonato ligand, preferably a water soluble salt of the ligand. Only one species of organothiosulfonato ligand is utilized in the reaction in order to obtain a symmetrical thiosulfonato Au(I) complex. Preferably the organothiosulfonato ligand has the formula $(A-SO_2S)^-_n M^{+n}$ wherein M, A, and n are as defined earlier for the organothiosulfonato Au(I) complex. Preferably M of the organothiosulfonato ligand is sodium or magnesium, with magnesium being most preferred. One suitable organothiosulfonate ligand is 4-methylphenylthiosulfonate potassium salt (AA). Another organothiosulfonate ligand is 4-methylphenylthiosulfonate magnesium salt (BB).

In another embodiment the Au(III) complex may be reacted directly with an excess of the above described organothiosulfato ligand. In this embodiment the organothiosulfato ligand is also acting as the reducing agent. Examples of preferred Au(III) complexes include $HAuCl_4$, $NaAuCl_4$, or $AuCl_3$. Again, it is preferred that the reaction be completed in an aqueous system.

The reactions may be done in a very broad temperature range, preferably ambient to 100° C., and more preferably 30 to 50° C. Generally, the reactions can take place in the natural pH of the system, and do not need adjustment. It is believed that a fairly neutral pH, of about 4 to 7.5 is preferable, with a pH of about 6 being most preferable. In most cases the reaction of the Au(I) complex or the Au(III) complex and the organothiosulfonato ligand takes place in just a few minutes at a temperature of 30° C., although this may differ depending on the reactants. It may be necessary to add a stabilizing electrolyte such as Cl$^-$ or Br$^-$ when utilizing particularly unstable Au(I) complexes.

Isolation of the resulting Au(I) product may be achieved by any suitable method, for example, by the treatment of the reaction mixture with several equivalents of an alkali or alkaline earth metal halide or by the addition of a non-solvent. The solid Au(I) complex may be collected by filtration and dried in vacuo. The preferred method of isolation typically involves the introduction of an alkali or alkaline earth metal halide followed by cooling of the reaction solution. The material is isolated by suction filtration. The procedure is straightforward with no complicated operations.

The compounds of the invention may be used to sensitize silver halide emulsions by the various techniques known to those skilled in the art. One suitable method includes adding the complexes to a silver halide emulsion as an aqueous solution and digesting the emulsion at a temperature in the range of 40 to 80° C.

The following examples are intended to illustrate, but not limit, the invention.

EXAMPLES

Example 1

Preparation of compound (I)

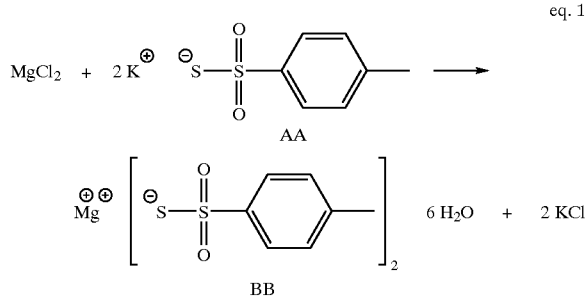

eq. 1

Synthesis of (BB) according to eq 1. To 100 mL of ethanol in an Erlenmeyer flask was added 4.8 g of MgCl$_2$. The mixture was stirred until a solution resulted. The MgCl$_2$ solution was then added to a suspension of 22.6 g of (AA) in 200 mL of ethanol. The mixture was stirred for 30 minutes at 55 C., and then allowed to cool to ambient temperature. The suspension was filtered to remove the resulting potassium chloride precipitate and the filtrate evaporated so that ca. 10 mL of a colorless solution remained. Finally, 200 mL of diethyl ether followed by 10 mL of acetone were added to the solution causing the immediate formation of a white solid. The solid was collected on a medium glass fritted funnel and dried in vacuo for four hours. The isolated yield was 21.2 g (84%). The isolated product's identity was confirmed by $^1$H nuclear magnetic resonance (NMR) spectroscopy, electrospray mass spectrometry and microanalysis: $^1$H NMR (D$_2$O) δ2.38 ppm (s, 3H), δ7.35 ppm (d 8 Hz, 2H), δ7.81 ppm (d 8 Hz, 2H); Electrospray MS (negative ion mode) M/Z=187, (TSS$^-$). Anal. Calc. For C$_{14}$H$_{26}$MgO$_{10}$S$_4$: C, 33.17%; H, 5.17%; S, 25.30%. Found: C, 33.12%; H, 4.88%; S, 25.39%.

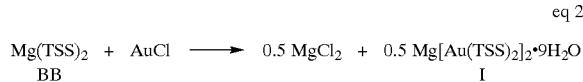

eq 2

The complex (I) was synthesized according to eq 2 by dissolving 3.78 g of (BB) in 5 mL of high purity water and filtering the mixture through a medium porosity glass fritted funnel. To the solution of (BB) was added 1.5 g of AuCl obtained from a commercial source. The resulting suspension was stirred rapidly for 5 minutes at 30 C. The suspension was filtered through 0.45μ glass membrane filter, and the resulting colorless solution was treated with 12.5 mL of a 5.1 M aqueous magnesium chloride solution. The reaction mixture was cooled for 1 hour in an ice bath. The solution above the resulting gummy oil was decanted and discarded. The gummy solid was extracted with acetone (2×20 mL), filtered through a 0.2μ Teflon membrane filter followed by solvent removal in vacuo. The resulting oil was treated with ca. 100 mL of methylene chloride, which immediately yielded a gelatinous solid. The solid was warmed under vacuum until 2.44 g (57%) of an off white solid was isolated. Compound I displays $^1$H NMR and mass spectra consistent with a material possessing the molecular structure illustrated above. $^1$H NMR (dmso-d$_6$) δ2.35 ppm (s, 3H), δ7.28 ppm (d 8 Hz, 2H), δ7.77 ppm (d 8 Hz, 2H); Electrospray MS (negative ion mode) M/Z=571 ([Au(TSS)$_2$]$^-$); Thermogravimetric analysis (TGA) and microanalysis confirm the presence of ca. 9 equivalents of water: TGA: ambient temperature to 150 C., 10.56% weight loss~9 equivalents of H$_2$O/ Mg[Au(TSS)$_2$]$_2$; Anal. Calc. For C$_{28}$H$_{46}$Au$_2$MgO$_{17}$S$_8$: C, 25.3%; H, 3.5%; S, 19.3%. Found: C, 25.17%; H, 3.19%; S, 19.10%.

Example 2

Preparation of (G)

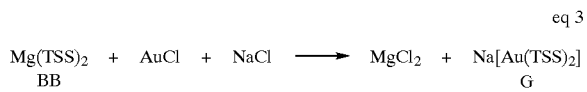

eq 3

The complex (G) was synthesized by dissolving 3.78 g of (BB) in 5 mL of high purity water and filtering the mixture through a medium porosity glass fitted funnel. To the solution of (BB) was added 1.5 g of AuCl. The resulting suspension was stirred rapidly for 5 minutes at 30° C. The suspension was filtered through a 0.45μ glass membrane filter and the resulting colorless solution treated with 5 mL of a saturated sodium chloride solution. Initially an oil formed that was crystallized after rapid stirring. The white solid was collected on a glass funnel and air-dried overnight. The isolated yield was 3.47 g (91%). The crude product was purified by dissolving 1 g of the solid in 20 mL of acetone. The solution was filtered through a 0.2μ Teflon membrane filter, and the acetone solvent was removed in vacuo. The resulting oil was dissolved in 20 mL of methylene chloride and the solvent was removed in vacuo. The process was repeated again, and the resulting solid was collected on a glass fitted funnel and air-dried. The isolated yield was 0.75 g (75%). Compound G displays $^1$H NMR and mass spectra and microanalyses consistent with a material possessing the molecular structure shown above: $^1$H NMR (D$_2$O) δ2.00 ppm (s, 3H), δ6.94 ppm (d 8 Hz, 2H), δ7.58 ppm (d 8 Hz, 2H); Electrospray MS (negative ion mode) M/Z=571 ([Au(TSS)$_2$]$^-$); Anal. Calc. For C$_{14}$H$_{14}$NaO$_4$S$_4$: C, 28.3%; H, 2.4%; S, 21.6%. Found: C, 28.80%; H, 2.48%; S, 21.56%.

Example 3

Preparation of Compound (H)

KAuCl$_4$+3 NaI→AuI$_3$+3 NaCl+KCl                              eq 4

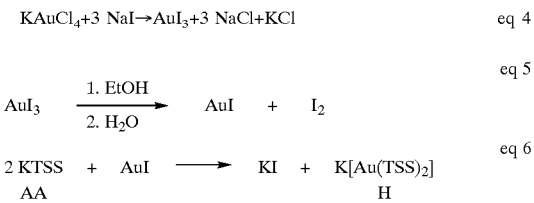

$$2 \text{ KTSS} + \text{AuI} \longrightarrow \text{KI} + \text{K[Au(TSS)}_2] \quad \text{eq 6}$$
$$\text{AA} \qquad\qquad\qquad\qquad\qquad \text{H}$$

In an Erlenmeyer flask, 5.0 g of KAuCl$_4$ was dissolved in 50 mL of high purity water and treated with 50 mL of high purity water containing 6.3 g of sodium iodide. The supernatant was discarded and the resulting insoluble AuI$_3$ was washed four times with 100 mL of high purity water. After the last water wash was decanted, the AuI$_3$ was washed nine times with 100 mL of ethanol. The resulting lemon yellow AuI solid was washed twice with 100 mL of high purity water yielding a lemon yellow solid in a minimum of high purity water after a final decantation. To 150 mL of high purity water was added 4.0 g of (AA). The resulting mixture was filtered to remove adventitious sulfur and transferred to a 500 mL beaker. The aqueous (AA) solution was heated to 40° C. and then treated with the AuI suspension prepared previously. The yellow color of the suspension was transformed to creamy white as the reaction progressed. Filtration of the suspension on a glass flitted funnel followed by drying in vacuo yielded the desired product in quantitative yield (7.6 g). The complex was recrystallized by extraction with acetone followed by precipitation by the addition of water. $^1$H NMR (dmso-d$_6$) δ2.36 ppm (s, 3H), δ7.29 ppm (d 8 Hz, 2H), δ7.79 ppm (d 8 Hz, 2H); Electrospray MS (negative ion mode) M/Z=571 ([Au(TSS)$_2$]$^-$); Anal. Calc. For C$_{14}$H$_{14}$KO$_4$S$_4$: C, 27.5%; H, 2.3%; S, 21.0%. Found: C, 27.49%; H, 2.34%; S, 21.13%.

Example 4

Alternative Preparation of Compound (I)

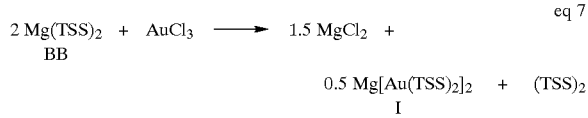

Although it is preferable to react an Au(I) complex with the organothiosulfonato ligand, it is also possible to utilize an Au(III) complex according to eq 7. The complex (I) was synthesized according to eq 7 by mixing 3.34 g of (BB) in 25 mL of absolute ethanol with 1 g of AuCl$_3$ in 25 mL of absolute ethanol. The reaction solution was analyzed by electrospray mass spectrometry which displayed a mass spectrum consistent with a material possessing the molecular structure illustrated above. Electrospray MS (negative ion mode) M/Z=571 ([Au(TSS)$_2$]).

The invention has been described in detail with particular reference to certain preferred embodiments thereof, but it will be understood that variations and modifications can be effected within the spirit and scope of the invention.

What is claimed is:

1. An organothiosulfonato Au(I) complex having the formula $$[A-SO_2S-Au-SSO_2-A]_n^- M^{+n}$$

wherein

M is a cationic counter ion;

A is a substituted or unsubstituted organic group;

and n is 1 to 4; and wherein the compound is symmetrical.

2. The organothiosulfonato Au(I) complex of claim 1 wherein A is a substituted or unsubstituted aliphatic, aromatic, or heterocyclic group.

3. The organothiosulfonato Au(I) complex of claim 2 wherein A is a substituted or unsubstituted aliphatic group having 1 to 20 carbon atoms, a substituted or unsubstituted aromatic group have from 6 to 20 carbon atoms, or a substituted or unsubstituted 3- to 1 5-membered heterocyclic ring with at least one atom selected from nitrogen, oxygen, sulfur, selenium, or tellurium.

4. The organothiosulfonato Au(I) complex of claim 3 wherein A is a substituted or unsubstituted aliphatic group having 1 to 8 carbon atoms, a substituted or unsubstituted aromatic group having from 6 to 10 carbon atoms, or a substituted or unsubstituted 5- to 6-membered heterocyclic ring with at least one atom selected from nitrogen.

5. The organothiosulfonato Au(I) complex of claim 4 wherein A is a substituted or unsubstituted aromatic group having from 6 to 10 carbon atoms.

6. The organothiosulfonato Au(I) complex of claim 1 wherein M is an alkali metal, alkaline earth metal, or ammonium cation.

7. The organothiosulfonato Au(I) complex of claim 4 wherein M is an alkali metal, alkaline earth metal, or ammonium cation.

8. The organothiosulfonato Au(I) complex of claim 6 wherein M is magnesium, lithium, sodium, potassium, rubidium, or cesium.

9. The organothiosulfonato Au(I) complex of claim 7 wherein M is magnesium, lithium, sodium, potassium, rubidium, or cesium.

10. The organothiosulfonato Au(I) complex of claim 1 wherein the organothiosulfonato Au(I) complex is sodium bis(4-methylphenylthiosulfonato)-aurate(I).

11. A method of manufacturing an organothiosulfonato Au(I) complex comprising reacting an Au(I) complex with an organothiosulfato ligand having the formula $$(A-SO_2S)^-_n M^{+n}$$

wherein M is a cationic counter ion, n is 1 to 4, and A is a substituted or unsubstituted organic group.

12. The method of claim 11 wherein the Au(I) complex is prepared by reducing an Au(III) compound with a stoichiometric amount of a reducing agent.

13. The method of claim 11 where the reaction is accomplished in aqueous media.

14. The method of claim 13 wherein the organothiosulfonato ligand is in the form of a water soluble salt.

15. The method of claim 14 wherein the M is an alkali metal, alkaline earth metal, or ammonium cation.

16. The method of claim 14 wherein M is sodium and magnesium.

17. The method of claim 16 wherein the Au(I) complex is AuCl$_2^-$AuBr$_2^-$, Au(MeS—CH$_2$—CH$_2$—CHNH$_2$COOH)$_2^+$, Au(MeS—CH$_2$—CH$_2$—CHNH$_2$)$_2{}^+$, Au(CNS)$_2{}^-$, Au(NH$_3$)$_2{}^+$, AuCl, or AuBr.

18. The method of claim 17 wherein the Au(I) complex is AuCl.

19. The method of claim 11 wherein A is a substituted or unsubstituted aliphatic group having 1 to 8 carbon atoms, a substituted or unsubstituted aromatic group having from 6 to 10 carbon atoms, or a substituted or unsubstituted 5- to 6-membered heterocyclic ring with at least one atom selected from nitrogen.

20. The method of claim 11 further comprising isolating the resulting organothiosulfonato Au(I) complex from the reaction mixture.

21. A method of manufacturing an organothiosulfonato Au(I) complex comprising reacting an Au(III) complex with an organothiosulfato ligand having the formula (A—SO$_2$S)$^-{}_n$M$^{+n}$ wherein M is a cationic counter ion, n is 1 to 4, and A is a substituted or unsubstituted organic group.

22. The method of claim 21 where the reaction is accomplished in aqueous media.

23. The method of claim 22 wherein the organothiosulfonato ligand is in the form of a water soluble salt.

24. The method of claim 23 wherein the M is an alkali metal, alkaline earth metal, or ammonium cation.

25. The method of claim 23 wherein M is sodium and magnesium.

26. The method of claim 25 wherein the Au(III) complex is HAuCl$_4$, NaAuCl$_4$, or AuCl$_3$.

27. The method of claim 21 wherein A is a substituted or unsubstituted aliphatic group having 1 to 8 carbon atoms, a substituted or unsubstituted aromatic group having from 6 to 10 carbon atoms or a substituted or unsubstituted 5- to 6-membered heterocyclic ring with at least one atom selected from nitrogen.

28. The method of claim 21 further comprising isolating the resulting organothiosulfonato Au(I) complex from the reaction mixture.

* * * * *